United States Patent
Schammel et al.

(10) Patent No.: US 7,378,544 B2
(45) Date of Patent: May 27, 2008

(54) ANTHRACENE AND OTHER POLYCYCLIC AROMATICS AS ACTIVATORS IN THE OXIDATION OF AROMATIC HYDROCARBONS

(75) Inventors: Wayne P. Schammel, Plainfield, IL (US); Victor A. Adamian, Naperville, IL (US); Yenamandra Viswanath, Naperville, IL (US); Igor V. Zakharov, Moscow (RU)

(73) Assignee: BP Corporation North America Inc., Warrenville, IL (US)

( * ) Notice: Subject to any disclaimer, the term of this patent is extended or adjusted under 35 U.S.C. 154(b) by 220 days.

(21) Appl. No.: 10/980,718

(22) Filed: Nov. 3, 2004

(65) Prior Publication Data

US 2005/0137420 A1 Jun. 23, 2005

Related U.S. Application Data

(60) Provisional application No. 60/530,759, filed on Dec. 18, 2003, provisional application No. 60/530,752, filed on Dec. 18, 2003.

(51) Int. Cl.
*C07C 51/255* (2006.01)
*B01J 31/02* (2006.01)
*B01J 31/26* (2006.01)

(52) U.S. Cl. .................. 562/412; 562/413; 562/416; 562/417

(58) Field of Classification Search ............... 562/412, 562/413, 416, 417
See application file for complete search history.

(56) References Cited

U.S. PATENT DOCUMENTS

| | | | |
|---|---|---|---|
| 2,833,816 A | 5/1958 | Saffer et al. ............... 260/524 |
| 3,855,252 A * | 12/1974 | Robinson et al. ........... 552/269 |
| 4,755,622 A | 7/1988 | Schammel et al. ......... 562/413 |
| 4,992,579 A | 2/1991 | Schammel .................. 562/413 |
| 5,095,143 A * | 3/1992 | Heberer et al. ............. 562/416 |
| 5,183,933 A | 2/1993 | Harper et al. ............... 562/414 |
| 2001/0041811 A1* | 11/2001 | Sikkenga et al. ........... 562/416 |
| 2005/0192459 A1* | 9/2005 | Metelski et al. ............ 562/416 |

FOREIGN PATENT DOCUMENTS

| | | |
|---|---|---|
| SU | 239936 | 8/1969 |
| WO | 37407 | 1/2000 |
| WO | 000779 A2 | 1/2005 |

OTHER PUBLICATIONS

I. V Zakharov: "Mechanism of Initiation and Inhibition by Mn(II) in Hydrocarbon Oxidation in the Presence of Colbalt-Manganese Bromide Catalyst", Kinetics and Catalysis, vol. 39, No. 4, 1998, pp. 485-492, XP009048069.

I. V. Zakharov: "Catalyzed Oxidation of 2-Ethylthiophene", Zhurnal Oschei Khimii Eng. Vers., vol. 44, No. 4, 1974, pp. 806-810, XP009048073.

Santamaria, J. et al.: Electron Transfer Activation—A Selective Photooxidation Method for the Preparation of Aromatic Aldehydes and Ketones:, Tetrahedron Lettters, Elsevier Science Publishers. Amsterdam, NL, vol. 32, No. 34, (Aug. 19, 1991) pp. 4291-4294, XP000218116.

* cited by examiner

*Primary Examiner*—Rosalynd Keys
(74) *Attorney, Agent, or Firm*—Kelly L. Cummings

(57) ABSTRACT

The present invention relates to the liquid phase oxidation of aromatic hydrocarbons in the presence of at least one heavy metal oxidation catalyst and bromine, which is activated by at least one of anthracene or another polycyclic aromatic compound to produce aromatic carboxylic acids.

37 Claims, No Drawings

ANTHRACENE AND OTHER POLYCYCLIC AROMATICS AS ACTIVATORS IN THE OXIDATION OF AROMATIC HYDROCARBONS

This application claims the benefit of U.S. Provisional Application No. 60/530,759 filed Dec. 18, 2003, and U.S. Provisional Application No. 60/530,752 filed Dec. 18, 2003, which are incorporated herein by reference in their entireties.

BACKGROUND OF THE INVENTION

The present invention relates to the liquid phase oxidation of aromatic hydrocarbons in the presence of at least one heavy metal oxidation catalyst and bromine, which is activated by anthracene or another polycyclic aromatic compound to produce aromatic carboxylic acids. The present invention includes the liquid phase oxidation of pseudocumene (PSC) (1,2,4-trimethylbenzene) in the presence of a catalyst comprising a multivalent catalyst, a source of bromine, and a polycyclic aromatic hydrocarbon, to produce trimellitic acid (TMLA). The present invention relates to the liquid phase oxidation of PSC in the presence of a catalyst comprising a multivalent metal oxidation catalyst, a source of bromine, and a polycyclic aromatic hydrocarbon selected from anthracene, naphthalene, tetracene, and combinations thereof to produce TMLA. Trimellitic acid can be dehydrated to produce trimellitic anhydride (TMA). TMA and TMLA are commercially valuable as the raw materials for manufacture of polyester materials. Trimellitate esters are used as plasticizers for polyvinyl chloride, especially for high performance wire and cable insulation as these have principle features of temperature stability and low volatility. Trimellitic anhydride is used in the production of resins for electrodeposition and powder coatings, and as a binder for glass fibers, sand, and other aggregates. Trimellitic anhydride is used as an embossing agent for vinyl flooring and as a curing agent for epoxy resins. It is also used as an intermediate for the synthesis of surface coatings chemicals, adhesives, polymers, dyes printing inks, pharmaceuticals and agrochemicals.

Aromatic carboxylic acids such as benzene dicarboxylic acids and naphthalene dicarboxylic acids are commercially valuable as the raw materials for manufacture of polyester materials which are used to manufacture fibers, films, resins, and many other petrochemical compounds. U.S. Pat. No. 2,833,816, hereby incorporated by reference, discloses the liquid phase oxidation of xylene isomers into corresponding benzene dicarboxylic acids in the presence of bromine using a catalyst having cobalt and manganese components. As described in U.S. Pat. No. 5,183,933 incorporated by reference herein in its entirety, liquid phase oxidation of dimethylnaphthalenes to naphthalene dicarboxylic acids can also be accomplished in the presence of bromine and a catalyst having cobalt and manganese components. Typically, aromatic carboxylic acids are purified in a subsequent process as described, for example, in U.S. Pat. No. 3,584,039, U.S. Pat. No. 4,892,972, and U.S. Pat. No. 5,362,908.

The liquid phase oxidation of aromatic hydrocarbons to aromatic carboxylic acids is conducted using a reaction mixture comprising aromatic hydrocarbons and a solvent. Typically, the solvent comprises a $C_1$-$C_8$ monocarboxylic acid, for example acetic acid, benzoic acid, or mixtures thereof with water. As used herein, "aromatic hydrocarbon" preferably means a molecule composed predominantly of carbon atoms and hydrogen atoms, and having one or more aromatic rings, particularly dimethyl benzenes, trimethyl benzenes, and dimethyl naphthalenes. Aromatic hydrocarbons suitable for liquid-phase oxidation to produce aromatic carboxylic acid generally comprise an aromatic hydrocarbon having at least one substituent group that is oxidizable to a carboxylic acid group. As used herein, "aromatic carboxylic acid" preferably means an aromatic hydrocarbon with at least one carboxyl group.

A bromine promoter and catalyst are added to the reaction mixture which is reacted in the presence of an oxidant gas. Typically, the catalyst comprises at least one suitable heavy metal component. Suitable heavy metals include heavy metals with atomic weight in the range of about 23 to about 178. Examples include cobalt, manganese, vanadium, molybdenum, nickel, zirconium, titanium, cerium or a lanthanide metal such as hafnium. Suitable forms of these metals include for example, acetates, hydroxides, and carbonates. The use of bromine in producing aromatic carboxylic acids by liquid phase oxidation improves conversion of the reactants.

USSR patent no. 239936 (I. V. Zakharov) discloses a method for the liquid-phase oxidation of alkyl-aromatic hydrocarbons with molecular oxygen in an acetic-acid solution in the presence of a catalyst—a cobalt salt and dibromoanthracene—at a temperature of 90-110° C., wherein, for the purpose of intensifying the process, a manganese salt addition in a volume of 1-3% of the cobalt salt concentration is introduced into the reaction mixture.

Quality of aromatic carboxylic acids is often determined by the concentration of intermediate products found as impurities in the aromatic carboxylic acid product. The type and concentration of these impurities varies with the types and concentrations of catalyst and promoter used and with the particular aromatic carboxylic acid product desired. The presence of such impurities may interfere with use of the carboxylic acid product or make it less desirable for certain purposes. For example, when terephthalic acid is used in a direct condensation process in preparing polyesters, impurities in the terephthalic acid can cause undesirable coloration of the polyester and can act as chain terminators.

It has been discovered that anthracene and other polycyclic aromatic hydrocarbons activate the oxidations of alkylaromatics to aromatic carboxylic acids even when added in very small amounts. This activation is reflected in increased oxygen uptake, temperature increases, lower intermediates and shortened reaction time and higher yield of primary product.

The addition of anthracene, naphthalene and other polycyclic aromatic hydrocarbons to the oxidation of alkylaromatics, such as, xylenes, trimethylbenzenes and dimethylnaphthalenes causes an unexpected and pronounced activation which can enhance the production of aromatic acids such as terephthalic acid (TA), isophthalic acid (IPA), trimellitic acid (TMLA), and naphthalene dicarboxylic acid (NDA). Higher activities in these oxidations (catalyzed by Co, Mn and Br) can lead to reduced intermediates and by-products, lower catalyst costs and reduced corrosion and emissions caused by Br. Very small levels of anthracene or other polycyclic aromatic hydrocarbon are needed to cause this activation. Using anthracene or another polycyclic aromatic hydrocarbon as an activator may reduce catalyst costs by enabling one to obtain good conversion of the starting aromatic hydrocarbon to the desired aromatic carboxylic acid with less catalyst metal. Being able to use less cobalt, for example, can produce a significant cost savings in the process.

The activation of the oxidation of aromatic hydrocarbons to aromatic carboxylic acids with polycyclic aromatics, such as anthracene, could result in significant decreases in catalyst concentration which would reduce catalyst cost significantly, especially if the amount of cobalt, which is the costliest component in the catalyst packages, can be decreased. The ability to use less catalyst is an unexpected advantage which can provide cost savings and a more economical process. This provides a particular cost saving advantage in those processes where recovery and recycling of expensive catalyst components, such as cobalt is difficult or not possible.

In addition, the use of anthracene to activate the oxidation of aromatic hydrocarbons to aromatic carboxylic acids may permit the oxidation process to be run at a lower temperature which means that less energy would have to be used in the process. This could also provide a cost savings and, in addition, using less energy is desirable from an environmental standpoint.

Another difficulty encountered in the liquid phase oxidation of aromatic hydrocarbons to form aromatic carboxylic acids is solvent and aromatic hydrocarbon burning. The liquid phase oxidation reaction typically results in the burning of at least 2% of the solvent and more than 2% of the aromatic hydrocarbon. We have discovered that the use of a polycyclic aromatic hydrocarbon as a promoter increases the yield of product aromatic carboxylic acid without detrimental increase in solvent and hydrocarbon burning.

SUMMARY OF THE INVENTION

The present invention relates to a process for oxidizing an aromatic hydrocarbon with a source of molecular oxygen to form an aromatic carboxylic acid under liquid phase conditions in the presence of a catalyst system comprising at least one suitable heavy metal, a source of bromine, and at least one polycyclic aromatic hydrocarbon. The invention includes a process for liquid-phase oxidation of pseudocumene to trimellitic acid, the process comprising oxidizing pseudocumene in the presence of a catalyst comprising at least one suitable heavy metal, a source of bromine, and at least one polycyclic aromatic hydrocarbon.

The present invention also relates to a catalyst system for producing an aromatic carboxylic acid by liquid-phase oxidation of aromatic hydrocarbons, the catalyst system comprising:
  a) at least one heavy metal oxidation catalyst;
  b) a source of bromine; and
  c) a polycyclic aromatic hydrocarbon.

The present invention also relates to a process for liquid-phase oxidation of pseudocumene to trimellitic acid in which the catalyst comprises at least one suitable heavy metal, a source of bromine, and anthracene.

The present invention further relates to a process for liquid-phase oxidation of pseudocumene to trimellitic acid at a temperature in the range of from about 50° C. to about 250° C. with a catalyst system which comprises at least one suitable heavy metal, a source of bromine, and at least one polycyclic aromatic hydrocarbon which is preferably selected from anthracene, naphthalene, tetracene, and mixtures thereof.

In the catalyst system of the invention, the polycyclic aromatic hydrocarbon may be anthracene, naphthalene, tetracene, and combinations thereof. Another source of polycyclic aromatic hydrocarbon can be heavier byproduct streams from petroleum refining which contain polycyclic aromatic hydrocarbons.

The heavy metal comprises cobalt and one or more secondary metals selected from manganese, cerium, zirconium, titanium and hafnium, and is present in an amount ranging from about 100 ppmw to about 6,000 ppmw. Typically, the atom ratio of elemental bromine to heavy metal ranges from about 0.1:1 to about 4:1; for example from about 0.2:1 to about 2:1; for example, from about 0.3:1 to about 1:1. The polycyclic aromatic hydrocarbon comprises anthracene, naphthalene, or tetracene, alone or in combination.

An embodiment of the invention relates to a process for oxidizing pseudocumene with an oxidant gas to form trimellitic acid in a reaction solvent comprising a $C_1$-$C_8$ monocarboxylic acid under liquid phase conditions at temperatures in the range from about 120° C. to about 250° C., the process comprising oxidizing pseudocumene in the presence of a catalyst comprising at least one suitable heavy metal, a source of bromine, and one or more polycyclic aromatic hydrocarbons.

The bromine source may comprise one or more bromine compounds selected from $Br_2$, HBr, NaBr, KBr, $NH_4Br$, benzyl-bromide, bromo acetic acid, dibromo acetic acid, tetrabromoethane, ethylene dibromide and bromoacetyl bromide.

The total bromine added can be from a single source of bromine, for example, ionic bromine sources (HBr, NaBr, $NH_4Br$ and the like) or from a combined form of bromine, for example, organic bromides such as benzyl bromide, tetrabromoethane and others.

The polycyclic aromatic hydrocarbon preferably comprises anthracene, naphthalene, or tetracene, or mixtures thereof, with anthracene being more preferred.

DESCRIPTION OF THE PREFERRED EMBODIMENT(S)

The present invention relates to the use of anthracene or another polycyclic aromatic hydrocarbon as a catalyst activator in processes which utilize the cobalt catalyzed oxidation of alkylaromatics. Specifically, paraxylene (PX) to terephthalic acid (TA) which is then purified to give purified terephthalic acid (PTA), metaxylene (MX) to isophthalic acid (IPA), pseudocumene (1,2,4-trimethylbenzene) to trimellitic acid (TMLA), and 2,6-dimethyl naphthalene (2,6-DMN) to 2,6-napthalene dicarboxylic acid (NDA). The increase in activity afforded by anthracene and similar compounds can be taken advantage of in a variety of ways depending on the product line.

The present invention includes a process for the oxidation of pseudocumene (PSC) with molecular oxygen to trimellitic acid (TMLA) under liquid-phase conditions in the presence of a catalyst system comprising a heavy metal oxidation catalyst, a source of bromine, and a polycyclic aromatic hydrocarbon activator.

Adding anthracene or another polycyclic aromatic hydrocarbon in the initial catalyst or continuously (i.e., in the tailout catalyst) enables one to obtain conversions of pseudocumene to trimellitic acid with low amounts of undesirable methyl diacid by-products when a lower amount of cobalt is used in the catalyst system. The activating effect of anthracene is more pronounced when the catalyst is added continuously in a tailout catalyst.

In one embodiments, the catalyst system comprises a cobalt-manganese-cerium-bromine catalyst and anthracene.

In another embodiment, the catalyst system comprises a cerium titanium-cobalt-manganese-bromine catalyst and anthracene. In another embodiment, the catalyst system comprises a cerium zirconium-cobalt-manganese-bromine catalyst and anthracene.

The present invention also provides a process for oxidizing aromatic hydrocarbons with an oxidant gas to form aromatic carboxylic acids in a reaction solvent comprising a $C_1$-$C_8$ monocarboxylic acid under liquid phase conditions at temperatures in the range from about 50 to about 250° C., for example, from about 100 to about 250° C., for example, from about 100° C. to about 200° C., for example, from about 120° C. to about 250° C., for example, from about 120° C. to about 210° C. Use of anthracene or another polycyclic hydrocarbon enables one to run the oxidation at lower temperatures, if desired.

The process comprises oxidizing aromatic hydrocarbons in the presence of a catalyst comprising at least one suitable heavy metal, bromine, and one or more polycyclic aromatic hydrocarbons. The heavy metal may comprise cobalt and one or more secondary metals selected from manganese, cerium, zirconium, titanium and hafnium. The heavy metal preferably is present in an amount ranging from about 100 ppmw to about 6000 ppmw, for example, from about 500 ppmw to about 3000 ppmw.

Oxidation is conducted at a pressure in the range from about 1 to about 40 kg/cm$^2$ gauge (about 15 psig to about 569 psig), for example, from about 90 psig to about 450 psig, for example, from about 90 psig to about 400 psig. The oxidation of DMN to NDA is conducted at a pressure of from about 300 to about 450 psig, preferably from about 350 to about 400 psig.

The aromatic hydrocarbons preferably comprise paraxylene, metaxylene, pseudocumene, and dimethylnaphthalene. The polycyclic aromatic hydrocarbons preferably comprise anthracene, naphthalene, tetracene, and mixtures thereof, with anthracene being more preferred. In some embodiments, using anthracene as an activator may reduce the catalyst requirements by up to about 75% so that less heavy metal can be used in the catalyst.

This invention provides a catalyst system for liquid-phase oxidation of aromatic hydrocarbons to form aromatic carboxylic acid at a temperature in the range from about 50° C. to about 250° C., for example, from about 100° C. to about 250° C., for example, from about 150° C. to about 200° C., for example, from about 120° C. to about 220° C.; for example, from about 170° C. to about 210° C., for example, from about 170° C. to about 200° C.

In one embodiment of the invention, wherein pseudocumene is oxidized to form trimellitic acid, the temperature is about 170° C. at the start of the oxidation and is increased until a reaction temperature of about 210°-220° C. is reached.

The pseudocumene oxidation is typically conducted at a pressure of about 90 psig to about 400 psig, for example, about 90 psig to about 300 psig, for example, about 100 psig 290 psig, for example, about 105 psig to 280 psig.

The amount of polycyclic compound used in the catalyst system may be from about 5 ppm to about 10,000 ppm, for example, from about 5 ppm to about 5,000 ppm, for example, from about 5 ppm to about 1000 ppm, for example, from about 5 ppm to about 200 ppm.

The catalyst system comprises at least one suitable heavy metal, a source of bromine, and one or more polycyclic aromatic hydrocarbons. Preferably the heavy metal and anthracene or other polycyclic aromatic hydrocarbon are present in a solvent comprising a $C_1$-$C_8$ monocarboxylic acid. The heavy metal preferably comprises cobalt and one or more secondary metals selected from manganese, cerium, zirconium, titanium and hafnium, and is preferably present in an amount ranging from about 100 ppmw to about 6,000 ppmw. Preferably, the atom ratio of elemental bromine to heavy metal ranges from about 0.1:1 to about 4:1, more preferably about 0.3:1 to about 1:1. The polycyclic aromatic hydrocarbon preferably comprises anthracene, naphthalene, tetracene, or mixtures thereof. Another source of polycyclic aromatic hydrocarbon can be polycyclic aromatic hydrocarbon-containing byproduct streams from petroleum refining.

The oxidation of aromatic hydrocarbons to aromatic carboxylic acids in the present invention is conducted at a pressure in the range from about 1 to about 40 kg/cm$^2$ gauge, for example, from about 5 to about 40 kg/cm$^2$ gauge, for example, from about 14 to about 32 kg/cm$^2$ gauge, for example, from about 22 to about 29 kg/cm$^2$ gauge. The aromatic hydrocarbons include, but are not limited to alkylaromatic hydrocarbons, preferably containing one through four methyl groups, such as paraxylene, metaxylene, pseudocumene, and dimethylnaphthalene. The polycyclic aromatic hydrocarbon is selected from anthracene, naphthalene, tetracene, and mixtures thereof. Another source of polycyclic aromatic hydrocarbon may be polycyclic aromatic hydrocarbon-containing byproduct streams from petroleum refining.

The present invention relates to a process for the oxidation of aromatic hydrocarbons with molecular oxygen to aromatic carboxylic acids under liquid-phase conditions in the presence of a catalyst activated by anthracene. In preferred embodiments, the catalyst is a cobalt-manganese-bromine catalyst activated by anthracene which may also contain additional metal additives.

This invention also provides a catalyst system for liquid-phase oxidation of aromatic hydrocarbons to form aromatic carboxylic acid at a temperature in the range from about 100° C. to about 250° C. The catalyst system comprises at least one suitable heavy metal, a source of bromine, and one or more polycyclic aromatic hydrocarbons. The bromine source preferably is one or more bromine compounds selected from $Br_2$, HBr, NaBr, KBr, $NH_4Br$, benzyl-bromide, bromo acetic acid, dibromo acetic acid, tetrabromoethane, ethylene dibromide and bromoacetyl bromide. Preferably the heavy metal, bromine source, and polycyclic aromatic hydrocarbon are present in a solvent comprising a $C_1$-$C_8$ monocarboxylic acid. The heavy metal preferably comprises cobalt and one or more secondary metals selected from manganese, cerium, zirconium and hafnium, and is preferably present in an amount ranging from about 100 ppmw to about 6,000 ppmw. Preferably, the atom ratio of elemental bromine to heavy metal ranges from about 0.1:1 to about 4:1, for example, from about 0.2:1 to about 2:1, for example, for example, from about 0.3:1 to about 1:1. The polycyclic aromatic hydrocarbon comprises anthracene, naphthalene, tetracene, or mixtures thereof.

In one embodiment of the invention, wherein pseudocumene is oxidized to trimellitic acid, the catalyst comprises one or more heavy metal oxidation catalysts comprising cerium, zirconium, cobalt, and manganese, and wherein the cerium content is about 9 to about 30 weight percent, the zirconium content is about 2 to about 5 weight percent, the manganese content is about 25 to about 40 weight percent, and the cobalt content is about 30 to about 70 weight percent, the amount of each metal present being given in weight percent of the total metals present; wherein a source of bromine is added to provide a total molar ratio of bromine added of about 30 to about 100 percent of the total metal catalyst present; and wherein a polycyclic aromatic hydrocarbon is added to provide about 5 ppm to about 10,000 ppm of polycyclic aromatic hydrocarbon, for example, from about 5 ppm to about 5,000 ppm of polycyclic aromatic hydrocarbon, for example, from about 5 ppm to about 1000 ppm of polycyclic aromatic hydrocarbon, for example, from about 5 ppm to about 200 ppm of polycyclic aromatic hydrocarbon.

Methods for the liquid phase oxidation of pseudocumene to TMLA using a multivalent catalyst and bromine promoter are described in U.S. Pat. No. 4,755,622 and U.S. Pat. No. 4,992,579, both of which are incorporated herein by reference in their entireties.

U.S. Pat. No. 4,755,622 discloses the liquid-phase oxidation of pseudocumene in the presence of a multi-valent catalyst promoted by a source of bromine wherein the oxidation is conducted in two steps so that the amount of bromine added in the first stage is about 10 to about 35 percent of the total bromine added and the remainder is added in the second stage.

U.S. Pat. No. 4,992,579 discloses the liquid-phase oxidation of pseudocumene (PSC) wherein the initial part of the reaction is conducted in a semi-continuous or batch mode followed by a batch tail-out wherein most of the bromine promoter and cerium in the plus three valence state is added in the batch tail-out stage, thus reducing the contact time of the polycarboxylic acid moieties with cobalt-manganese-bromine or zirconium-cobalt-manganese-bromine catalysts and improving the yield of trimellitic acid (TMLA) from PSC.

One embodiment of the present invention relates to a process for converting pseudocumene to trimellitic acid, which comprises catalytically oxidizing a pseudocumene-containing feedstock with a source of molecular oxygen under liquid-phase conditions in the presence of a catalyst comprising a source of cobalt, a source of manganese plus a source of bromine, and a polycyclic aromatic hydrocarbon, with or without a source of zirconium, at a temperature in the range of about 100° C. to about 250.° C., and in two stages, wherein the first stage is conducted batchwise or semi-continuously and the second stage is conducted batchwise, wherein addition of the bromine component is conducted so that about 10 to about 35 percent by weight of the total bromine is added in the first stage and the remainder is added in the second stage, wherein the temperature in the second stage is upward from about 175° C. to about 250° C. and the temperature in the first stage is between about 125°. C. and about 165° C., wherein the two stage addition of the bromine component is conducted while the source of molecular oxygen is introduced to the feedstock.

Another embodiment of the present invention relates to a process for the oxidation of pseudocumene with molecular oxygen to trimellitic acid under liquid-phase conditions in the presence of a catalyst comprising one or more heavy metal oxidation catalysts comprising cerium having a valence of plus three, zirconium, cobalt and manganese to provide from about 3 to about 10 milligram atoms total metals per gram mole of pseudocumene, a source of bromine, and a polycyclic aromatic hydrocarbon, at a temperature in the range of about 100° C. to about 275° C., the process comprising the staged addition of the bromine component in at least two stages wherein 0 to about 35 percent by weight of the total bromine is added in the first stage and the remainder is added in the last stage, and wherein all the cerium is added in the last stage, and wherein the temperature in the last stage is upward from about 175° C. to about 275° C., and the temperature in the preceding stage is between about 125° C. and about 165° C.

The liquid-phase oxidation of aromatic hydrocarbons to produce aromatic carboxylic acids can be conducted as a batch process, a continuous process, or a semi-continuous process. The oxidation reaction can be conducted in one or more reactors. A reaction mixture is formed by combining an aromatic hydrocarbon feed, solvent, heavy metal oxidation catalyst, a source of bromine, and a polycyclic aromatic hydrocarbon activator. In a continuous or semi-continuous process, the reaction mixture components preferably are combined in a mixing vessel before being introduced into the oxidation reactor, however, the reaction mixture can be formed in the oxidation reactor.

Aromatic carboxylic acids for which the invention is suited include mono- and polycarboxylated species having one or more aromatic rings and which can be manufactured by reaction of gaseous and liquid reactants in a liquid phase system, and especially those in which solid reaction products are produced and/or liquid components of the reaction mixture enter a vapor phase above the liquid phase in the reactor. Examples of aromatic carboxylic acids for which the invention is particularly suited include trimesic acid, isophthalic acid, terephthalic acid, benzoic acid and naphthalene dicarboxylic acids.

Suitable aromatic hydrocarbon feed generally comprises an aromatic hydrocarbon having at least one group that is oxidizable to a carboxylic acid group. The oxidizable substituent or substituents can be an alkyl group, such as a methyl, ethyl or isopropyl group. It also can be a group already containing oxygen, such as a hydroxyalkyl, formyl or keto group. The substituents can be the same or different. The aromatic portion of feedstock compounds can be a benzene nucleus or it can be bi- or polycyclic, such as a naphthalene nucleus. The number of oxidizable substituents on the aromatic portion of the feedstock compound can be equal to the number of sites available on the aromatic portion, but is generally fewer than all such sites, preferably 1 to about 4 and more preferably 1 to 3. Examples of useful feed compounds include toluene, ethylbenzene, o-xylene, p-xylene, m-xylene, 1-formyl-4-methylbenzene, 1-hydroxymethyl-4-methylbenzene, 1,2,4-trimethylbenzene, 1-formyl-2,4-dimethylbenzene, 1,2,4,5-tetramethylbenzene, alkyl-, hydroxymethyl-, formyl- and acyl-substituted naphthalene compounds, such as 2,6- and 2,7-dimethylnaphthalenes, 2-acyl-6-methylnaphthalene, 2-formyl-6-methylnaphthalene, 2-methyl-6-ethylnaphthalene and 2,6-diethylnaphthalene.

For manufacture of aromatic carboxylic acids by oxidation of corresponding aromatic hydrocarbon pre-cursors, e.g., manufacture of isophthalic acid from meta-disubstituted benzenes, terephthalic acid from para-disubstituted benzenes, trimellitic acid from 1,2,4-trimethylbenzene, naphthalene dicarboxylic acids from disubstituted naphthalenes, it is preferred to use relatively pure feed materials, and more preferably, feed materials in which content of the pre-cursor corresponding to the desired acid is at least about 95 wt. %, and more preferably at least 98 wt. % or even higher. A preferred aromatic hydrocarbon feed for use to manufacture terephthalic acid comprises paraxylene. A preferred feed for making isophthalic acid comprises metaxylene. A preferred feed for making trimellitic acid comprises pseudocumene. A preferred feed for making 2,6-naphthalene dicarboxylic acid is 2,6-dimethylnaphthalene. Toluene is a preferred feed material for making benzoic acid.

In one embodiment of the invention, the liquid-phase oxidation of pseudocumene to produce trimellitic acid can be conducted as a batch process, a continuous process, or a semicontinuous process. The oxidation reaction can be conducted in one or more reactors. A reaction mixture is formed by combining a pseudocumene feed, solvent, catalyst, a bromine promoter, and a polycyclic aromatic hydrocarbon promoter. In a continuous or semicontinuous process, the reaction mixture components preferably are combined in a mixing vessel before being introduced into the oxidation reactor, however, the reaction mixture can be formed in the oxidation reactor.

Solvents comprising an aqueous carboxylic acid, and especially a lower alkyl (e.g., $C_1$-$C_8$) monocarboxylic acid, for example acetic or benzoic acid, are preferred because they tend to be only sparingly prone to oxidation under typical oxidation reaction conditions used for manufacture of aromatic acids, and can enhance catalytic effects in the oxidation. Examples of such carboxylic acids include acetic acid, propionic acid, butyric acid, benzoic acid and mixtures thereof. Ethanol and other co-solvent materials which oxidize to monocarboxylic acids under the aromatic acid oxidation reaction conditions also can be used as is or in combination with carboxylic acids with good results. For purposes of overall process efficiency and minimizing separations, it is preferred that when using a solvent comprising a mixture of monocarboxylic acid and such a co-solvent, the co-solvent should be oxidizable to the monocarboxylic acid with which it is used.

Catalysts used according to the invention comprise materials that are effective to catalyze oxidation of the aromatic hydrocarbon feed to aromatic carboxylic acid. Preferably, the catalyst is soluble in the liquid oxidation reaction body to promote contact among catalyst, oxygen and liquid feed; however, heterogeneous catalyst or catalyst components may also be used. Typically, the catalyst comprises at least one suitable heavy metal component such as a metal with atomic weight in the range of from about 23 to about 178. Examples of suitable heavy metals include cobalt, manganese, vanadium, molybdenum, chromium, iron, nickel, zirconium, titanium, cerium, or a lanthanide metal such as hafnium. Suitable forms of these metals include for example, acetates, hydroxides, and carbonates. The catalyst of this invention preferably comprises cobalt compounds alone or in combination with one or more of manganese compounds, cerium compounds, zirconium compounds, titanium compounds, or hafnium compounds.

A bromine promoter is used to promote oxidation activity of the catalyst metal, preferably without generation of undesirable types or levels of by-products, and is preferably used in a form that is soluble in the liquid reaction mixture. Conventional bromine promoters include $Br_2$, HBr, NaBr, KBr, $NH_4Br$, and organic bromides.

We have discovered that anthracene and other polycyclic compounds, such as naphthalene and tetracene (2,3,-benzanthracene), are effective as activators for the liquid-phase oxidation of hydrocarbons to produce aromatic carboxylic acids. The liquid-phase oxidation of aromatic hydrocarbons to form aromatic carboxylic acids can be carried out in the presence of a promoter comprising anthracene, naphthalene or tetracene and a metal catalyst, preferably comprising cobalt and either manganese, cerium, or other metal additives.

The addition of anthracene, naphthalene and/or other polycyclic aromatic hydrocarbons to the homogeneous oxidation of alkylaromatics such as xylenes, and dimethylnaphthalenes cause an unexpected and pronounced activation which can enhance the production of aromatic acids such as terephthalic acid (TA), isophthalic acid (IPA), trimellitic acid/anhydride (TMLA/TMA) and naphthalene dicarboxylic acid (NDA). Higher activities in these oxidations (catalyzed by Co, Mn and Br) can lead to reduced intermediates and by-products and lower catalyst costs. Very small levels of the polycyclic aromatic hydrocarbon are needed to cause this activation.

Depending on the particular reaction, anthracene or another polycyclic aromatic hydrocarbon may be added initially, in a batch oxidation, continuously in continuous oxidation, in the tailout catalyst, in batch oxidation or both batch and tailout modes. The amount of activating effect may vary with concentration of anthracene or other polycyclic aromatic hydrocarbon activator and with the mode of addition. For some reactions, the use of anthracene as a catalyst activator may permit the use of a lower reaction temperature or may allow the amount of catalyst metal, particularly cobalt, to be decreased. For some reactions, if the catalyst system is already operating at its optimum, anthracene may not further increase the catalyst activity; however, in these systems, anthracene does exhibit an activating effect when the reaction is operated at less than optimal conditions, such as with a lower temperature or less catalyst metal. This has the advantageous effect of lowering the cost of the process operation.

The oxidation reaction is conducted in an oxidation reactor. The oxidation reactor can comprise one or more reactor vessels. Oxidant gas is also introduced into the oxidation reactor. Oxidant gas used according to the invention comprises molecular oxygen. Air is conveniently used as a source of molecular oxygen. Oxygen-enriched air, pure oxygen and other gaseous mixtures comprising at least about 5% molecular oxygen also are useful. Such oxygen-enriched sources containing at least about 10% molecular oxygen are advantageous. As will be appreciated, as molecular oxygen content of the source increases, compressor requirements and handling of inert gases in reactor off-gases are reduced.

Proportions of the feed, catalyst, oxygen and solvent are not critical to the invention and vary not only with choice of feed materials and intended product but also choice of process equipment and operating factors. Solvent to feed weight ratios suitably range from about 1:1 to about 10:1. Oxidant gas typically is used in at least a stoichiometric amount based on feed but not so great that unreacted oxygen escaping from the liquid body to the overhead gas phase forms a flammable mixture with other components of the gas phase. Catalysts suitably are used in concentrations of catalyst metal, based weight of aromatic hydrocarbon feed and solvent, greater than about 100 ppmw, preferably greater than about 500 ppmw, and less than about 10,000 ppmw, preferably less than about 6,000 ppmw, more preferably less than about 3000 ppmw. Bromine promoter preferably is present in an amount such that the atom ratio of bromine to catalyst metal suitably is greater than about 0.1:1, preferably greater than about 0.2:1, preferably greater than about 0.3:1 and suitably is less than about 4:1, preferably less than about 3:1. In accordance with this invention the promoter comprises one or more polycyclic aromatic hydrocarbons in combination with conventional bromine promoters, in an amount such that the atom ratio of bromine to catalyst metal most preferably ranges from about 0.25:1 to about 2:1.

Pressure in the reaction vessel is at least high enough to maintain a substantial liquid phase comprising feed and solvent in the vessel. Generally, pressures of about 5 to about 40 kg/cm$^2$ gauge are suitable, with preferred pressures for particular processes varying with feed and solvent compositions, temperatures and other factors. Solvent residence times in the reaction vessel can be varied as appropriate for given throughputs and conditions, with about 20 to about 150 minutes being generally suited to a range of processes.

As will be appreciated by those skilled in the manufacture of aromatic acids, preferred conditions and operating parameters vary with different products and processes and can vary within or even beyond the ranges specified above.

Aromatic carboxylic acid product recovered from the liquid can be used or stored as is, or it may be subjected to purification or other processing. Purification is beneficial for removing by-products and impurities that may be present with the aromatic carboxylic acid that is recovered. For aromatic carboxylic acids such as terephthalic and isophthalic acids, purifications preferably involves hydrogenation of the oxidation product, typically dissolved in water or other aqueous solvent, at elevated temperature and pressure in the presence of a catalyst comprising a metal with hydrogenation catalytic activity, such as ruthenium, rhodium, platinum or palladium, which typically is supported on carbon, titania or other suitable, chemically-resistant supports or carriers for the catalyst metal. Purification processes are known, for example, from U.S. Pat. No. 3,584,039, U.S. Pat. Nos. 4,782,181, 4,626,598 and U.S. Pat. No. 4,892,972. If purification is conducted with water as solvent, washing with water to remove residual oxidation solvent from the solid aromatic carboxylic acid can be carried out as an alternative to drying. Such washing can be accomplished using suitable solvent exchange devices, such as filters, as disclosed in U.S. Pat. No. 5,679,846, U.S. Pat. No. 5,175,355 and U.S. Pat. No. 5,200,557.

Typically, mother liquor is separated from the aromatic carboxylic acid product through separation techniques known in the art, for example, filtration, centrifuge, or combinations of known methods. It is preferable to recycle at least a portion of the mother liquor and commercial operations typically recycle a significant portion of the mother liquor.

It has been found that when 2,6-naphthalenedicarboxylic acid (NDA) is produced by MC-oxidation of 2,6-dimethylnaphthalene (DMN), under some conditions, anthracene addition increases the NDA yield by about 2 wt %. An increase of 2 wt % is significant in a commercial operation.

It appears that anthracene addition allows running the oxidation process at mild conditions that are not practical otherwise and the resultant benefits are higher NDA yields. Running at milder conditions may have the advantage of being less costly.

The ability to reduce cobalt in the catalyst is particularly helpful in the oxidation of DMN to NDA. Since oxidation of DMN to NDA is more difficult than oxidation of pX to TA, a significantly higher amount of expensive oxidation catalyst metals is used to produce NDA. Use of anthracene or another polycyclic aromatic hydrocarbon as an activator for the oxidation of DNM to NDA may have the advantage of reducing costs by allowing the use of less catalyst metal, by enabling one to run the reaction at milder condition and/or by lowering burning of DMN and acetic acid.

It has also been found that when 2,6-naphthalenedicarboxylic acid (NDA) is produced by MC-oxidation of 2,6-dimethylnaphthalene (DMN), and the NDA yield is at the optimum value, the addition of anthracene did not increase the yield of NDA. It may be that the oxidation reaction is operating at its optimum activity and selectivity at the chosen conditions and is not further stimulated by the addition of anthracene.

In the case of oxidation of DMN to produce NDA, the activating effect of anthracene was seen with continuous addition of anthracene, but was not seen when anthracene was added to the initial reaction mixture.

In the production of trimellitic acid from pseudocumene lower catalyst costs may be achieved due to the ability to use less cobalt in the catalyst. Less burning of acetic acid solvent and the pseudocumene feed occurs with anthracene which also provides a cost savings.

The use of anthracene or another suitable polycyclic aromatic hydrocarbon as an activator increases the rate of oxidation and enables the pseudocumene oxidation reaction to operate at a lower temperature which means lower burning of acetic acid, better color, and better selectivity towards products. A better color product can be achieved with lower temperature and lower cobalt.

Anthracene and other polycyclic compounds, such as naphthalene and tetracene (2,3,-benzanthracene), are effective as activators for the liquid-phase oxidation of pseudocumene to produce trimellitic acid. The liquid-phase oxidation of pseudocumene to form trimellitic acid can be carried out in the presence of an activator comprising a polycyclic compound, preferably selected from anthracene, naphthalene, tetracene, or combinations thereof, and a metal catalyst, preferably comprising cobalt and either manganese, cerium, or both, along with a source of bromine. When anthracene or another polycyclic compound is used as a promoter, the amount of cobalt in the catalyst can be reduced to levels that are two to three times lower than the amount of cobalt used when there is no polycyclic activator compound in the catalyst system, resulting in yields and conversions comparable to those obtained in reactions using a conventional amount of cobalt.

In one embodiment, the process of the present invention comprises the oxidation of pseudocumene with molecular oxygen to trimellitic acid under liquid-phase conditions in the presence of a zirconium-cobalt-manganese-cerium-bromine catalyst or a cobalt-manganese-cerium-bromine catalyst and anthracene as a catalyst activator.

Each of Zr, Mn, and Co can be conveniently used as its acetate when pseudocumene is oxidized in the presence of acetic acid solvent. Zirconium is available on a commercial basis as a solution of $ZrO_2$ in acetic acid and, as such, is ideally suited for liquid-phase oxidations using acetic acid as reaction solvent. when cerium is a component of the catalyst, the cerium is preferably added in the tail-out reaction. Suitable cerium compounds having a valence of plus three must be soluble in the tail-out solution and they include cerium carbonate and cerium acetate. The source of molecular oxygen for the enhanced oxidation of this invention can vary in $O_2$ content from that of air to oxygen gas. Air is the preferred source of molecular oxygen for oxidations conducted at temperatures of 120° C. and above up to 275° C. For oxidation conducted with molecular oxygen, the preferred temperatures are in the range of 100° C. to 200° C. The minimum pressure for such oxidations is that pressure which will maintain a substantial liquid phase of 70-80 percent of the reaction medium, either neat pseudocumene, or pseudocumene and 70-80 percent of the acetic acid. The acetic acid solvent, when used, can suitably ranges from 1 to 10 parts on a weight basis per part of the pseudocumene. The pseudocumene and/or acetic acid not in the liquid phase because of vaporization by heat of reaction is advantageously condensed and the condensate returned to the oxidation as a means for removing heat and thereby temperature controlling the exothermic oxidation reaction. Such vaporization of pseudocumene reactant and/or acetic acid solvent is also accompanied by vaporization of lower boiling by-product water. When it is desired to take advantage of the benefits of withdrawing acetic acid and water of reaction from the liquid-phase oxidation, condensate is not returned to the oxidation.

The source of molecular oxygen for the enhanced oxidation can vary in $O_2$ content from that of air to oxygen gas. Air is the preferred source of molecular oxygen for oxidations conducted at temperatures of 120° C. and above up to 275° C. For oxidation conducted with molecular oxygen, the preferred temperatures are in the range of 100° C. to 200° C. The minimum pressure for such oxidations is that pressure which will maintain a substantial liquid phase of 70-80 percent of the reaction medium, either neat pseudocumene (PSC), or PSC and 70-80 percent of the acetic acid. The acetic acid solvent, when used, can amount to 1-10 parts on a weight basis per part of the PSC. The PSC and/or acetic acid not in the liquid phase because of vaporization by heat of reaction is advantageously condensed and the condensate returned to the oxidation as a means for removing heat and thereby temperature controlling the exothermic oxidation reaction. Such vaporization of PSC reactant and/or acetic acid solvent is also accompanied by vaporization of lower boiling by-product water. When it is desired to take advantage of the benefits of withdrawing acetic acid and water of reaction from the liquid-phase oxidation, as will be hereinafter demonstrated, condensate is not returned to the oxidation.

Proportions of the feed, catalyst, oxygen and solvent are not critical to the invention and vary not only with choice of feed materials and intended product but also choice of process equipment and operating factors. Solvent to feed weight ratios suitably range from about 1:1 to about 10:1. Oxidant gas typically is used in at least a stoichiometric amount based on feed but not so great that unreacted oxygen escaping from the liquid body to the overhead gas phase forms a flammable mixture with other components of the gas phase. Catalysts suitably are used in concentrations of catalyst metal, based on weight of aromatic hydrocarbon feed and solvent, greater than about 100 ppmw, preferably greater than about 500 ppmw, and less than about 10,000 ppmw, preferably less than about 6,000 ppmw, more preferably less than about 3000 ppmw. Use of anthracene as an activator may lower the cobalt requirement by up to about 75% enabling one to use less cobalt in the catalyst metals and to use less catalyst metals overall.

Bromine promoter preferably is present in an amount such that the atom ratio of bromine to catalyst metal suitably is greater than about 0.1:1, preferably greater than about 0.3:1 and suitably is less than about 4:1, preferably less than about 1:1. In accordance with this invention the source of bromine is present in an amount such that the atom ratio of bromine to catalyst metal most preferably ranges from about 0.3:1 to about 1:1.

Acetic acid or aqueous acetic acid is a preferred solvent, with a solvent to feed ratio of from about 1:1 to about 5:1, for example, from about 1.8:1 to about 4:1, for example, from about 1.5:1 to about 3:1. The catalyst preferably comprises cobalt in combination with manganese, cerium, zirconium, titanium, hafnium, or any combination thereof. A source of bromine is preferably used as promoter. The catalyst is suitably present in amounts providing about 600 ppmw to about 2500 ppmw of catalyst metals based on weight of the aromatic hydrocarbon and solvent. The bromine promoter most preferably is present in an amount such that the atom ratio of bromine to catalyst metal ranges from about 0.3:1 to about 1:1.

Trimellitic acid product recovered from the liquid can be used or stored as is, or it may be subjected to purification or other processing. Purification is beneficial for removing by-products and impurities that may be present with the aromatic carboxylic acid that is recovered. Typically, mother liquor is separated from the aromatic carboxylic acid product through separation techniques known in the art, for example, filtration, centrifuge, or combinations of known methods.

The examples which follow illustrate the invention in more detail. The following Examples will serve to illustrate certain specific embodiments of the herein disclosed invention. These Examples should not, however, be construed as limiting the scope of the novel invention contained herein as there are many variations which may be made thereon without departing from the spirit of the disclosed invention, as those of skill in the art will recognize.

EXAMPLES 1-5

Oxidation of Meta-Xylene to Isophthalic Acid: Experimental Procedure and Results Experiments were conducted in a 300 mL titanium Parr mini-reactor. Initial reactor charge contained catalyst and 76 g of 95% acetic acid (HOAc). Reactor was pressurized to 400 psig under $N_2$ and heated to a desired temperature. After desired temperature has been reached, nitrogen atmosphere was switched to a continuous flow of 8 vol % $O_2$ in $N_2$. After reactor was saturated with 8% $O_2$ (as determined by level of $O_2$ in vent gas), 25 to 30 mL of MX were pumped in over 60 minutes oxidation time. At the same time, additional 25 mL of HOAc were continuously added over the same time period. Anthracene was added either to the initial reactor charge (referred to as batch addition) or was continuously added as a solution in HOAc over a period of oxidation (60 minutes). After 60 min, 8% $O_2$ was switched to nitrogen, reactor cooled down to room temperature, contents of reactor removed and submitted for HPLC analysis. Vent gas was continuously analyzed during oxidation for $O_2$, $CO_2$, CO. Vent gas was also sampled two or three times during each experiment and analyzed for volatile organic compounds using in-lab GC. In all examples catalyst in the initial charge consisted of: $Co(OAc)_2.4H_2O$=0.264 g; Mn(OAc) 2.4H2O=0.278 g; 48% HBr=0.240 g. In Examples 2 and 4, anthracene (AC) was added as a saturated solution (0.12-0.14 wt % AC) in 95/5 wt % $HOAc/H_2O$. In Example 5, AC (0.300 g) was added to the initial reactor charge.

Effect of anthracene was explored using a typical Co—Mn—Br oxidation catalyst at two different temperatures 180° C. and 195° C. with two modes of anthracene addition (continuous and batch). The results are shown in Table 1.

TABLE 1

| Example | Comments | T, °C. | Molar Yield, % | | | | MeBr, ppm |
| --- | --- | --- | --- | --- | --- | --- | --- |
| | | | IPA | 3-CBA | m-Toluic Acid | COx/MX (burning) | |
| 1 | Control No anthracene | 180 | 73 | 0.70 | 2.5 | 0.21 | 3 |
| 2 | Anthracene continuous | | 92 | 1.7 | 5.6 | 0.21 | 4 |
| 3 | Anthracene batch | | 80 | 0.6 | 2.2 | 0.23 | 4 |
| 4 | Control No anthracene | 195 | 91 | 0.30 | 1.0 | 0.58 | 19 |
| 5 | Anthracene continuous | | 89 | 0.25 | 0.8 | 0.60 | 23 |

Discussion of the Experimental Results:

Effect of Anthracene (AC) on IPA Yield

Continuous addition of anthracene to the oxidation of MX results in unexpected improvement in the yield of a product IPA. Comparison of Examples 1 and 2 shows that continuous addition of AC results in an increase of IPA yield from 73 to 92 mol %. This increase in IPA yield does not result in the increase in burning, which is an additional unexpected advantageous effect.

The effect of anthracene addition on IPA yield may vary with the temperature of oxidation. The effect is smaller at higher temperatures (assuming that the experimental conditions are otherwise identical). While very significant effect is seen at 180° C. (Examples 1 and 2), no improvement was seen at 195° C. (See Examples 3 and 4). It may be that at the higher temperatures the oxidation reaction is already operating at optimum conditions.

Anthracene Allows One to Run Oxidation at Lower Temperature

Comparison of control experiments at 180° C. and 195° C. (Examples 1 and 4) shows that oxidation at 180° C. gives much lower IPA yield (73%) than oxidation at 195° C. (91%). Therefore, to achieve high IPA yield, commercial oxidation is run at 190-200° C. However, oxidation at higher temperatures results in significantly higher burning losses and high levels of methyl bromide (MeBr)—a regulated ozone-depleting compound. As seen from Examples 1 and 4, the oxidation with continuous addition of anthracene at 180° C. results in higher IPA yield (92%) than oxidation without AC at 195° C. (91%). At the same time, burning at 180° C. is approximately ⅓ of the burning at 190° C. MeBr formation at 180° C. is reduced by 80% compared to 195° C. Therefore, addition of anthracene allows one to lower temperature of oxidation without losing IPA yield, to reduce burning losses and to reduce MeBr formation.

Effect of Batch Addition of Anthracene

Example 3 shows that anthracene can be added in batch mode. Addition of 0.3 g of anthracene (or 0.4 wt % in the initial charge) results in the increase in IPA yield from 73 to 80 mol %.

Small Amount of Anthracene Needed

Only a small amount of anthracene is needed to improve the oxidation reaction. In Examples 2 and 5 total amount of anthracene fed in 60 minutes was 0.06 mol % of the amount of MX. In Example 3, batch-loaded anthracene was 0.6 mol % of the MX fed.

EXAMPLES 6 AND 7

Oxidation of Para-xylene to Terephthalic Acid

Experiments are conducted in a 300 mL titanium Parr mini-reactor. Initial reactor charge contained catalyst and 100 g of 95% HOAc. Reactor was pressurized to 400 psig under $N_2$ and heated to 170° C. After desired temperature has been reached, nitrogen atmosphere is switched to a continuous flow of 8 vol % $O_2$ in $N_2$. After reactor is saturated with 8% $O_2$ (as determined by level of $O_2$ in vent gas), feedstock (paraxylene) is pumped in at a rate of 0.5 mL/min for 60 min. After 60 min, 8% $O_2$ is switched to nitrogen, and the reactor is cooled down to room temperature, total reactor effluent (TRE) is removed and submitted for HPLC analysis. Vent gas is continuously analyzed for $O_2$, $CO_2$, CO. Vent gas is also sampled two or three times during each experiment and analyzed for volatile organic compounds using in-lab gas chromatography (GC).). In examples 6, and 7, catalyst in the initial charge consisted of: $Co(OAc)_2.4H_2O$=0.400 g; $Mn(OAc)2.4H2O$=0.115 g; 48% HBr=0.127 g. In Example 7, AC (0.300 g) was added to the initial reactor charge.

TABLE 2

| Example | Comments | Molar Yield, % | | | |
| --- | --- | --- | --- | --- | --- |
| | | TA | 4-CBA | p-Toluic Acid | COx/PX (burning) |
| 6 | Control No anthracene | 24 | 5 | 22 | 0.08 |
| 7 | Anthracene batch | 44 | 7 | 29 | 0.08 |

DISCUSSIONS OF EXAMPLES 6 AND 7

Examples 6 and 7 represent oxidation of p-Xylene to TA at 170° C.

Control experiment (Example 6, no anthracene) shows that the yield of TA is 24 mol % at a burning level of 0.08. Batch addition of 0.3 wt % of anthracene to the initial reactor charge resulted in the increase of TA yield to 44 mol %, while the burning remained at 0.08. Thus, examples 6 and 7 illustrate that anthracene improves the oxidation of p-xylene to TA and that this improvement does not increase detrimental burning.

EXAMPLES 8-14

Oxidation of 2,6-dimethylnaphthalene (DMN) to Produce 2,6-naphthalenedicarboxylic Acid (NDA) with Continuous Addition of Anthracene The reactor was charged with the desired amount of cobalt acetate, manganese acetate, and HBr. Water was added to the initial charge to adjust the concentration of water at the end of reaction to 8-10%. About 108 ml of glacial acetic acid was also placed in the initial reactor charge. During the run 18 ml of acetic acid solvent and 27 gms of DMN were added to the reactor over 60 minutes. The oxygen source was 8 mole % $O_2$. Two sources of anthracene solutions were used in the experiments. A solution containing 1750 ppmw anthracene was prepared by saturating glacial acetic acid with anthracene at 72° F. (22.2° C.). Another solution containing 530 ppmw was prepared by saturating a 95/5 (wt/wt) acetic acid/water solution with anthracene at 72° F. (22.2° C.).

These two sources of anthracene were used to control the amount of anthracene added to the oxidation reactor. Example 8 was a control run with no anthracene added to the reaction mixture. In Examples 9 and 10, anthracene was added only to initial reactor charge with no further anthracene addition during the oxidation run. In Examples 11 and 12, glacial acetic acid saturated with anthracene at 72° F. was used as the solvent for the reactor initial charge and also as solvent added continuously during the oxidation run. In Example 13, the reactor initial charge contained no anthracene, but the glacial acetic acid saturated with anthracene at 72° F. was added continuously during the oxidation run. In Example 14, the reactor initial charge contained no anthracene, but 95/5 acetic acid/water mixed solvent saturated with anthracene at 72° F. was added continuously during the oxidation run.

The actual amounts of anthracene present in the different experiments is shown in Table 3.

TABLE 3

|  | Ex. 8 | Ex. 9 | Ex. 10 | Ex. 11 | Ex. 12 | Ex. 13 | EX. 14 |
| --- | --- | --- | --- | --- | --- | --- | --- |
| Description | Base Case (Control) | Base Case with anthracene in initial charge | Base Case with anthracene in initial charge but 20% less Co | Base Case with continuous anthracene addition | Base Case with cont anthracene addition but 30% less Co | Base Case with cont. anthracene addition | Base Case with/ cont. anthracene addition |
| Catalyst | Fresh | Fresh + anthracene in initial charge | Fresh + anthracene in initial charge | Fresh + anthracene in initial charge + added continuously | Fresh w/30% less cobalt + anthracene in initial charge + added continuously | Fresh + anthracene added continuously | Fresh + anthracene added continuously |
| Anthracene in initial charge | No | Yes | Yes | Yes | Yes | No | No |
| Anthracene concentration in reactor solvent, ppmw | 0 | 3650 | 3650 | 1622 | 1622 | 230 | 70 |
| Solvent Ratio (g/g) | 4.7 | 4.7 | 4.7 | 4.7 | 4.7 | 4.7 | 4.7 |
| Initial Reactor Charge |  |  |  |  |  |  |  |
| Co Acetate (g) | 1.3737 | 1.3742 | 1.0995 | 1.3743 | 0.9618 | 1.3739 | 1.3741 |
| Mn Acetate (g) | 0.4507 | 0.4502 | 0.3605 | 0.4506 | 0.4506 | 0.4506 | 0.4506 |
| 48% HBr (g) | 0.6196 | 0.6197 | 0.4962 | 0.6197 | 0.6198 | 0.6202 | 0.6198 |
| Water (g) | 3.9753 | 3.9749 | 4.1452 | 3.9752 | 3.9480 | 3.9751 | 3.975 |
| Acetic Acid g) | 108.70 | 108.70 | 108.87 | 108.70 | 108.70 | 108.7 | 108.7 |
| Other (g) |  | 0.5002 | 0.5003 |  |  |  |  |
| Reaction Conditions |  |  |  |  |  |  |  |
| Total DMN added (g) | 27.00 | 27.00 | 27.00 | 27.00 | 27.00 | 27.00 | 27.00 |
| Total HOAc Injected (g) | 18.00 | 18.00 | 18.00 | 18.00 | 18.00 | 18.00 | 18.00 |
| Feed Gas O2 Conc. (vol %) | 7.96 | 8.00 | 8.00 | 8.00 | 8.00 | 8.00 | 8.00 |

TABLE 3-continued

|  | Ex. 8 | Ex. 9 | Ex. 10 | Ex. 11 | Ex. 12 | Ex. 13 | EX. 14 |
|---|---|---|---|---|---|---|---|
| Reaction Time (minutes) | 60 | 60 | 60 | 60 | 60 | 60 | 60 |
| Slurry Weight (g) | 158.60 | 156.50 | 153.10 | 152.50 | 157.40 | 155.5 | 156.2 |
| Average Temperature (deg. F.) | 407° F. (208.3° C.) | 407° F. (208.3° C.) | 407° F. (208.3° C.) | 407° F. (208.3° C.) | 407° F. (208.3° C.) | 407° F. (208.3° C.) | 407° F. (208.3° C.) |
| Average Pressure (psig) | 353 | 350 | 350 | 350 | 350 | 351 | 351 |
| Average Inlet Gas Flow (scfh) | 7.96 | 10.58 | 8.68 | 9.95 | 10.75 | 10.17 | 10.17 |
| Average Vent Gas Flow (scfh) | 7.60 | 10.17 | 8.30 | 9.53 | 10.28 | 9.81 | 9.80 |
| Net Yield, (mole %) |  |  |  |  |  |  |  |
| TMLA | 1.69 | 2.41 | 1.43 | 2.35 | 1.91 | 2.69 | 2.57 |
| FNA | 0.40 | 0.76 | 2.20 | 0.49 | 0.43 | 0.48 | 0.62 |
| 2-NA | 0.71 | 0.53 | 0.45 | 0.42 | 0.46 | 1.12 | 1.16 |
| 2-Me-6-NA | 0.04 | .45 | 1.64 | 0.07 | 0.10 | 0.14 | 0.25 |
| 2,6-NDA | 75.98 | 76.55 | 69.48 | 74.44 | 82.35 | 84.46 | 86.71 |

The results of Examples 8-12 show that anthracene addition allows one to lower cobalt addition and may also increase NDA yield when anthracene is added continuously along with use of lower amount of cobalt in the catalyst system.

In Examples 8 and 9, anthracene in the initial charge did not produce a benefit.

In Example 10, a combination of lower cobalt and anthracene in the initial charge did not produce a benefit.

In Example 11, at base case cobalt concentration, continuous anthracene addition did not produce a benefit.

In Example 12, at 30% less cobalt concentration and continuous anthracene addition, the 2,6-NDA yield increased from 76 mole % to 82.3 mole %, which is a significant increase in product yield.

Effect of Anthracene Concentration

In Examples 8, 13, and 14 all oxidation conditions were at the Base Case values, except for the amount of anthracene added continuously to the oxidation reactor. In all these examples there was no anthracene present in the reactor initial charge. 2,6-NDA yield increased from 76 mole % to 86.7 mole % at 70 ppmw anthracene addition. However at a higher anthracene addition value of 230 ppmw, the 2,6-NDA yield decreased to 84.5 mole %. Obviously the concentration of anthracene in the reactor solvent affects the 2,6-NDA yield. The optimal anthracene concentration appears to be dependent on whether it is present in the initial charge or if it is added continuously during the run and it also depends on the concentrations of cobalt, manganese, and bromine in the reaction mixture and the reaction temperature.

In Example 11, anthracene was present at a concentration of 1392 in the initial reactor charge and 230 ppmw additional anthracene was added continuously during the run. However in Example 13, no anthracene was present in the initial reactor charge, but 230 ppmw anthracene was added continuously during the run. Because of the high initial concentration of anthracene, the 2,6-NDA yield was only 74.4 mole % in Example 11 compared to 84.5 mole % for Example 13. This clearly demonstrates that a high initial anthracene in the reactor prior to oxidation decreases the 2,6-NDA yield at the Base Case conditions.

Examples of Liquid Phase Oxidation of Pseudocumene (PSC)

Comparative Example A

Charge 0.87 g cobalt acetate tetrahydrate, 1.74 g manganese acetate tetrahydrate, 0.29 g hydrogen bromide solution (48%), and 0.086 g of zirconyl acetate solution (17% Zr) to a 2 liter titanium autoclave with 529 g glacial acetic acid, 28 g water, and 293 g pseudocumene.

This initial charge is heated to 320° F. (160° C.) under a slow nitrogen purge and then pressurized air (enriched to 24.5% $O_2$) was added at 54 standard cubic feet per hour for about 15 minutes. During this first 15 minute stage, the temperature was maintained at 330° F. (165.6° C.) by keeping the pressure at about 105 psig. Three minutes after adding the air, a tailout catalyst solution was added at 0.8 g/min until 40.0 g had been added. The tailout solution was made up by mixing 328 g acetic acid, 60 g water, 1.31 g manganese acetate tetrahydrate, 0.91 g Zirconium Solution, 12.39 g HBr Solution, and 2.10 g Cerium acetate.

Beginning at 15 minutes into the oxidation, the pressure and temperature were increased linearly from 345° F. (173.9° C.) and 105 psig to 410° F. (210° C.) and 280 psig respectively. The final temperature and pressure was reached at about 40 minutes into the oxidation. The temperature and pressure were then maintained at these levels until the Vent oxygen rapidly rose to 14% indicating the completion of the oxidation.

In addition to the temperature and pressure ramps, the air rate was stepped up from 54 to 60 SCFH from minute 15 to minute 20. It was kept at 58 SCFH until minute 45 and then was gradually stepped down to 50 SCFH over a 7 minute period. The air rate was kept at 50 SCFH until the oxidation was complete. The air is ramped in this manner to maximize oxygen consumption and to keep the vent oxygen from rising to the flammable range.

The product of this oxidation was collected, a sample was dried to solids and analyzed. Table 4 has the relevant data from this run and from Examples 15 and 16.

EXAMPLE 15

This oxidation was conducted in an identical fashion to Comparative Example A except that 0.5 g of anthracene was added to the initial reaction mixture.

EXAMPLE 16

This oxidation was conducted in an identical fashion to Comparative Example A except that the tailout catalyst was saturated with anthracene at 320 ppm and none was added into the initial catalyst.

TABLE 4

| Component, wt % of solids | Comparative Example A No Anthracene | Example 15 0.5 g Anthracene initial | Example 16 320 ppm anthracene in tailout catalyst |
|---|---|---|---|
| Trimellitic acid | 86.2 | 90.5 | 92.9 |
| Methyl diacids | 4.36 | 1.17 | 0.31 |
| Reaction time, (minutes) | 58.2 | 56.0 | 58.7 |

Table 4 shows the activating effect of anthracene, both when it is added initially and when it is added via the tailout catalyst (i.e., added continuously at a low level throughout the batch oxidation). The yield of trimellitic acid (TMLA) is higher because the prime intermediates, methyl diacids (also known as methyl dibasic acids or MDBs), are decreased markedly as a result of the higher activity.

The reaction used cobalt at levels that were 2-3 times lower than the usual commercial concentrations indicating that anthracene has the potential to provide a method for reducing catalyst costs substantially. The concentration of cobalt in Comparative Example A, Example 15, and Example 16 is 0.07 wt % based on pseudocumene charged. In a typical commercial reaction, the concentration of cobalt is 0.16 wt %. Therefore, comparing the results of Examples 15 and 16 with the results of Comparative Example A, it can be seen that adding anthracene in the initial or tailout catalyst enables one to obtain good conversions of pseudocumene to trimellitic acid with low amounts of methyl diacid by-products when a lower amount of cobalt (i.e., 0.07 wt %) is used in the catalyst system. The lower amount of cobalt used in the above examples represents a 56% reduction in cobalt compared to the typical 0.16 wt % of cobalt. Being able to reduce the cobalt by this much while maintaining acceptable activity could result in significant savings in catalyst cost.

That which is claimed is:

1. A process for oxidizing an aromatic hydrocarbon with a source of molecular oxygen to form an aromatic carboxylic acid selected from isophthalic acid, terephthalic acid, trimellitic acid, and 2,6-naphthalene dicarboxylic acid under liquid phase conditions in the presence of a catalyst comprising:

a) at least one heavy metal oxidation catalyst;
b) a source of bromine; and
c) an unsubstituted polycyclic aromatic hydrocarbon.

2. The process of claim 1 wherein the unsubstituted polycyclic aromatic hydrocarbon is selected from anthracene, naphthalene, tetracene, and combinations thereof.

3. The process of claim 2 wherein the unsubstituted polycyclic aromatic hydrocarbon is anthracene.

4. The process of claim 1 wherein the bromine source comprises one or more bromine compounds selected from $Br_2$, HBr, NaBr, KBr, $NH_4Br$, benzyl-bromide, bromo acetic acid, dibromo acetic acid, tetrabromoethane, ethylene dibromide, and bromoacetyl bromide.

5. The process of claim 1 wherein the heavy metal comprises cobalt and one or more secondary metals selected from manganese, cerium, zirconium, titanium vanadium, molybdenum, nickel, and hafnium.

6. The process of claim 1 wherein the heavy metal is present in an amount ranging from about 100 ppmw to about 6000 ppmw.

7. The process of claim 1 wherein the oxidation is conducted at a temperature in the range of from about 50° C. to about 250° C.

8. The process of claim 1 wherein the oxidation is conducted at a temperature in the range of from about 120° C. to about 250° C.

9. The process of claim 1 wherein oxidation is conducted at a pressure in the range of about of from about 90 psig to about 450 psig.

10. The process of claim 1 wherein oxidation is conducted at a pressure in the range of about of from about 100 psig to about 400 psig.

11. A process according to claim 1 for oxidizing paraxylene with a source of molecular oxygen to form terephthalic acid under liquid phase conditions in the presence of a catalyst comprising:

a) at least one heavy metal oxidation catalyst;
b) a source of bromine; and
c) an unsubstituted polycyclic aromatic hydrocarbon.

12. The process of claim 11 wherein the unsubstituted polycyclic aromatic hydrocarbon is selected from anthracene, naphthalene, tetracene, and combinations thereof.

13. The process of claim 12 wherein the unsubstituted polycyclic aromatic hydrocarbon is anthracene.

14. A process according to claim 1 for oxidizing metaxylene with a source of molecular oxygen to form isophthalic acid under liquid phase conditions in the presence of a catalyst comprising:

a) at least one heavy metal oxidation catalyst;
b) a source of bromine; and
c) an unsubstituted polycyclic aromatic hydrocarbon.

15. The process of claim 14 wherein the unsubstituted polycyclic aromatic hydrocarbon is selected from anthracene, naphthalene, tetracene, and combinations thereof.

16. The process of claim 15 wherein the unsubstituted polycyclic aromatic hydrocarbon is anthracene.

17. A process according to claim 1 for oxidizing 2,6-dimethylnaphthalene with a source of molecular oxygen to form 2,6-naphthalenedicarboxylic acid under liquid phase conditions in the presence of a catalyst comprising:

a) at least one heavy metal oxidation catalyst;
b) a source of bromine; and
c) an unsubstituted polycyclic aromatic hydrocarbon.

18. The process of claim 17 wherein the unsubstituted polycyclic aromatic hydrocarbon is selected from anthracene, naphthalene, tetracene, and combinations thereof.

19. The process of claim 18 wherein the unsubstituted polycyclic aromatic hydrocarbon is anthracene.

20. A process according to claim 1 for oxidizing pseudocumene to trimellitic acid, which comprises catalytically oxidizing a pseudocumene-containing feedstock with a source of molecular oxygen under liquid-phase conditions in the presence of a catalyst comprising:
   a) at least one heavy metal oxidation catalyst;
   b) a source of bromine; and
   c) an unsubstituted polycyclic aromatic hydrocarbon.

21. The process of claim 20 wherein the unsubstituted polycyclic aromatic hydrocarbon is selected from anthracene, naphthalene, tetracene, and combinations thereof.

22. The process of claim 21 wherein the unsubstituted polycyclic aromatic hydrocarbon is anthracene.

23. The process of claim 20 wherein the heavy metal comprises cobalt and one or more secondary metals selected from manganese, cerium, zirconium, titanium and hafnium.

24. The process of claim 20 wherein the heavy metal is present in an amount ranging from about 100 ppmw to about 6000 ppmw.

25. A process according to claim 20 for converting pseudocumene to trimellitic acid, which comprises catalytically oxidizing a pseudocumene-containing feedstock with a source of molecular oxygen under liquid-phase conditions in the presence of a catalyst comprising:
   a) a cobalt-manganese-cerium catalyst;
   b) a source of bromine; and
   c) anthracene.

26. A process according to claim 20 for converting pseudocumene to trimellitic acid, which comprises catalytically oxidizing a pseudocumene-containing feedstock with a source of molecular oxygen under liquid-phase conditions in the presence of a catalyst comprising:
   a) a zirconium-cobalt-manganese-cerium catalyst;
   b) a source of bromine; and
   c) anthracene.

27. The process of claim 20 wherein the oxidation is conducted at a temperature in the range of about 50° C. to about 250° C.

28. The process of claim 20 wherein the oxidation is conducted at a temperature in the range of about 100° C. to about 250° C.

29. The process of claim 20 wherein oxidation is conducted at a pressure in the range of about of about 90 psig to about 300 psig.

30. A process for converting pseudocumene to trimellitic acid, which comprises catalytically oxidizing a pseudocumene-containing feedstock with a source of molecular oxygen under liquid-phase conditions in the presence of a catalyst comprising:
   a) at least one heavy metal oxidation catalyst;
   b) a source of bromine; and
   c) an unsubstituted polycyclic aromatic hydrocarbon selected from anthracene, naphthalene, tetracene, and combinations thereof;
   at a temperature in the range of about 100° C. to about 250° C.; and at a pressure in the range of about of about 90 psig to about 300 psig.

31. The process of claim 30 wherein the oxidation is conducted at a temperature in the range of about 170° C. to about 220° C. and a pressure in the range of about of about 105 psig to about 280 psig, and wherein the unsubstituted polycyclic aromatic hydrocarbon is anthracene.

32. The process of claim 30 wherein the heavy metal comprises cobalt and one or more secondary metals selected from manganese, cerium, zirconium, titanium, and hafnium, and wherein the heavy metal is present in an amount ranging from about 100 ppmw to about 6000 ppmw.

33. A process according to claim 1 for converting pseudocumene to trimellitic acid, which comprises catalytically oxidizing a pseudocumene-containing feedstock with a source of molecular oxygen under liquid-phase conditions in the presence of a catalyst comprising a source of cobalt, a source of manganese plus a source of bromine, and an unsubstituted polycyclic aromatic hydrocarbon, with or without a source of zirconium, at a temperature in the range of about 100° C. to about 250° C., and in two stages, wherein the first stage is conducted batchwise or semi-continuously and the second stage is conducted batchwise, wherein addition of the bromine component is conducted so that about 10 to about 35 percent by weight of the total bromine is added in the first stage and the remainder is added in the second stage, wherein the temperature in the second stage is upward from about 175° C. to about 250° C. and the temperature in the first stage is between about 125° C. and about 165° C., wherein the two stage addition of the bromine component is conducted while the source of molecular oxygen is introduced to the feedstock.

34. The process of claim 33 wherein the unsubstituted polycyclic aromatic hydrocarbon is selected from anthracene, naphthalene, tetracene, and combinations thereof.

35. A process according to claim 1 for the oxidation of pseudocumene with molecular oxygen to trimellitic acid under liquid-phase conditions in the presence of a catalyst comprising one or more heavy metal oxidation catalysts comprising cerium having a valence of plus three, zirconium, cobalt and manganese to provide from about 3 to about 10 milligram atoms total metals per gram mole of pseudocumene, a source of bromine, and an unsubstituted polycyclic aromatic hydrocarbon, at a temperature in the range of about 100° C. to about 275° C., the process comprising the staged addition of the bromine component in at least two stages wherein 0 to about 35 percent by weight of the total bromine is added in the first stage and the remainder is added in the last stage, and wherein all the cerium is added in the last stage, and wherein the temperature in the last stage is upward from about 175° C. to about 275° C., and the temperature in the preceding stage is between about 125° C. and about 165° C.

36. The process of claim 35 wherein the unsubstituted polycyclic aromatic hydrocarbon is selected from anthracene, naphthalene, tetracene, and combinations thereof.

37. The process of claim 1 wherein the unsubstituted polycyclic aromatic hydrocarbon comprises an unsubstituted polycyclic aromatic hydrocarbon-containing petroleum refining byproduct stream.

* * * * *